United States Patent

Fischer et al.

[11] Patent Number: 5,883,277
[45] Date of Patent: Mar. 16, 1999

[54] METALLOCENE COMPLEXES WITH CATIONIC BRIDGES

[75] Inventors: David Fischer, Gönnheim; Franz Langhauser, Bad Dürkheim; Günther Schweier, Friedelsheim, all of Germany; Hans-Herbert Brintzinger, Taegerswilen, Switzerland; Nadine Leyser, Konstanz, Germany

[73] Assignee: BASF Aktiengesellschaft, Ludwigshafen, Germany

[21] Appl. No.: 894,238

[22] PCT Filed: Feb. 14, 1996

[86] PCT No.: PCT/EP96/00619

§ 371 Date: Aug. 14, 1997

§ 102(e) Date: Aug. 14, 1997

[87] PCT Pub. No.: WO96/26211

PCT Pub. Date: Aug. 29, 1996

[30] Foreign Application Priority Data

Feb. 24, 1995 [DE]  Germany .................. 195 06 557.3

[51] Int. Cl.⁶ .............. C07F 17/00; C07F 9/00; C07F 7/08; C08F 4/642
[52] U.S. Cl. ................ 556/53; 556/1; 556/21; 556/22; 556/23; 556/30; 556/41; 556/47; 556/53; 556/54; 556/56; 556/58; 556/351; 556/352; 556/943; 526/127; 526/160; 526/170; 526/172; 502/103; 502/117; 502/152; 534/15; 564/281; 568/9
[58] Field of Search ................. 556/1, 21, 22, 556/23, 30, 41, 47, 53, 54, 56, 58; 534/15; 526/160, 943, 127, 170, 172, 351, 352; 502/103, 117; 564/281; 568/9

[56] References Cited

FOREIGN PATENT DOCUMENTS 344 887  12/1989  European Pat. Off. .

OTHER PUBLICATIONS

G. K. Anderson et al., Organometallics 7, 1988, pp. 2285–2288.
Ch. Quian et al., J. Chem. Soc. Dalton Trans, 1993, pp. 3441–3445.
Ch. Quian et al., J. Organomet. Che. 445, 1993, pp. 79–84.
Monatshefte fur Chemie 144, 243–247 (1983).

*Primary Examiner*—Porfirio Nazario-Gonzalez
*Attorney, Agent, or Firm*—Keil & Weinkauf

[57] ABSTRACT

Metallocene complexes having a cationic bridge of the formula

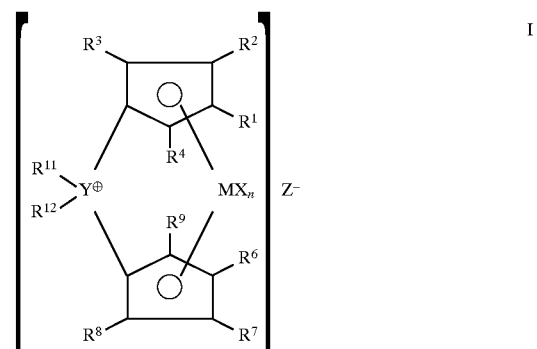

where the substituents have the following meanings:

M is a metal of transition group III, IV, V or VI of the Periodic Table of the Elements or a metal of the lanthanide group, X is fluorine, chlorine, bromine, iodine, hydrogen, $C_1$–$C_{10}$-alkyl, $C_6$–$C_{15}$-aryl or —$OR^5$, $R^1$ to $R^{12}$, Y, Z and n having the meanings set out in the specification, said complexes can be prepared via ligand systems of the formula II

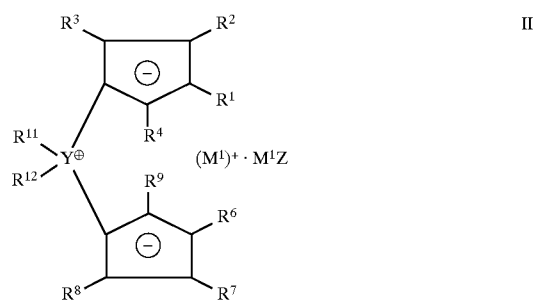

as intermediates.

5 Claims, No Drawings

METALLOCENE COMPLEXES WITH CATIONIC BRIDGES

This application was filed as a request for U.S. examination under 35 U.S.C. §371 of International application No. PCT/EP96/00619 filed Feb. 14, 1996.

The present invention relates to metallocene complexes of the formula I

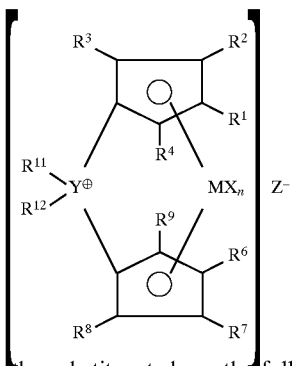

where the substituents have the following meanings:

M is a metal of transition group III, IV, V or VI of the Periodic Table of the Elements or a metal of the lanthanide group, X is fluorine, chlorine, bromine, iodine, hydrogen, $C_1$–$C_{10}$-alkyl, $C_6$–$C_{15}$-aryl or —$OR^5$, where $R^5$ is $C_1$–$C_{10}$-alkyl, $C_6$–$C_{15}$-aryl, alkylaryl, arylalkyl, fluoroalkyl or fluoroaryl each having from 1 to 10 carbon atoms in the alkyl radical and from 6 to 20 carbon atoms in the aryl radical, $R^1$ to $R^4$
and
$R^6$ to $R^9$ are hydrogen, $C_1$–$C_{10}$-alkyl, 5- to 7-membered cycloalkyl which may in turn bear $C_1$–$C_{10}$-alkyls as substituents, $C_6$–$C_{15}$-aryl or arylalkyl, where two adjacent radicals may also together form a cyclic group having from 4 to 15 carbon atoms, or $Si(R^{10})_3$ where $R^{10}$ is $C_1$–$C_{10}$-alkyl, $C_6$–$C_{15}$-aryl or $C_3$–$C_{10}$-cycloalkyl, Y is nitrogen, phosphorus, arsenic, antimony or bismuth, $R^{11}$, $R^{12}$ are hydrogen, $C_1$–$C_{10}$-alkyl, $C_3$–$C_{10}$-cycloalkyl or $C_6$–$C_{15}$-aryl, n is 0, 1 or 2 and $Z^-$ is a halide, carboxylate, monosubstituted sulfonate, borate or alkoxide.

The present invention further relates to ligand systems of the formula II

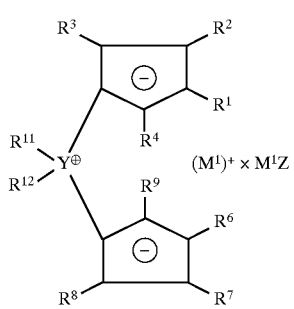

and also processes for preparing such metallocene complexes I and ligand systems II, the use of the ligand systems II for preparing the metallocene complexes I and to the use of the metallocene complexes I as catalysts for the polymerization of alkanes.

Bridged metallocene complexes in which elements of main group IV of the Periodic Table of the Elements function as a bridge are known, for example from EP-A 344 887 and are used as catalysts for the polymerization of alkenes.

However, the bridge is here restricted to neutral bridge atoms without the possibility of subsequent functionalization directly on the bridging atom. Furthermore, it is not possible to electronically influence the ligand system by introduction of a charge directly in the bridge.

G. K. Anderson et al., Organometallics 7 (1988), 2285–2288 discloses the introduction of phosphorus as bridging element between two cyclopentadienyl ligands. Ch. Qian et al., J. Chem. Soc. Dalton Trans. (1993), 3441–3445 and Ch. Qian et al., J. Organomet. Chem. 445 (1993), 79–84 describe nitrogen as a bridge in metallocene complexes. However, this has the disadvantage that the bridging element interacts with the metal of the metallocene complex or with other coordinatively unsaturated substrates.

It is an object of the present invention to provide metallocene complexes which do not have the disadvantages mentioned and which make possible, in particular, a very variable structure and possibly functionalization directly on the bridging atom.

We have found that this object is achieved by the metallocene complexes I defined in the introduction.

In addition, the present invention provides ligand systems II and also processes for preparing such metallocene complexes I and ligand systems II, and provides for the use of the ligand systems II for preparing the metallocene complexes I and the use of the metallocene complexes I as catalysts for the polymerization of alkenes.

Among the novel metallocene complexes of the formula I

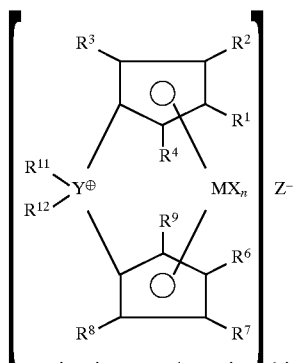

preference is given to those in which the substituents have the following meaning:

M is a metal of transition group IV of the Periodic Table of the Elements, viz. titanium, zirconium or hafnium, or a metal of the lanthanide group, but in particular zirconium or hafnium, X is halogen, in particular chlorine, or $C_1$–$C_{10}$-alkyl, in particular $C_1$–$C_4$-alkyl, where in the case of a plurality of radicals X these can also be different, $R^1$ to $R^4$ and $R^6$ to $R^9$ are hydrogen, $C_1$–$C_{10}$-alkyl, $C_6$–$C_{15}$-aryl, in particular linear or branched $C_1$–$C_6$-alkyl, or two adjacent radicals can together form a cyclic group having from 4 to 12 carbon atoms, Y is nitrogen or phosphorus, and $R^{11}$, $R^{12}$ are hydrogen, $C_1$–$C_{10}$-alkyl, $C_6$–$C_{15}$-aryl, in particular linear or branched $C_1$–$C_4$-alkyl, and the two radicals $R^{11}$ and $R^{12}$ are preferably identical.

Particular preference is given to metallocene complexes I which have a symmetric structure, ie. $R^1$ and $R^6$, $R^2$ and $R^7$, $R^3$ and $R^8$ as well as $R^4$ and $R^9$ are in each case identical.

The anion Z⁻ can in principle be selected without restriction. Anions which have been found to be particularly useful are halides, in particular iodide, carboxylates, in particular halogenated carboxylates such as trifluoroacetate, monosubstituted sulfonates, in particular aryl-substituted sulfonates such as p-toluenesulfonate, borates, in particular phenylborates such as tetrakispentafluorophenylborate or methyltrispentafluorophenylborate, and also alkoxides, in particular bulky alkoxides such as isopropoxides or tert-butoxides.

Particularly preferred metallocene complexes I are:

[P,P-diphenyl-1,1'-phosphoniumdiylbis(2-methyl-4-tert-butylcyclopentadienyl)zirconium dichloride] iodide,

[P-methyl-P-phenyl-1,1'-phosphoniumdiylbis(2-methyl-4-tert-butylcyclopentadienyl)zirconium dichloride] iodide,

[P,P-dimethyl-1,1'-phosphoniumdiylbis(2-methylindenyl)zirconium dichloride] iodide,

[P,P-diphenyl-1,1'-phosphoniumdiylbis(2-methylindenyl)zirconium dichloride] iodide,

[P-methyl-P-phenyl-1,1'-phosphoniumdiylbis(2-methylindenyl)zirconium dichloride] iodide,

[P,P-dimethyl-1,1'-phosphoniumdiylbis(2-methylbenzindenyl)zirconium dichloride] iodide,

[P,P-diphenyl-1,1'-phosphoniumdiylbis(2-methylbenzindenyl)zirconium dichloride] iodide,

[P-methyl-P-phenyl-1,1'-phosphoniumdiylbis(2-methylbenzindenyl)zirconium dichloride] iodide,

[P,P-dimethyl-1,1'-phosphoniumdiylbis(2-methylbenzindenyl)hafnium dichloride] iodide,

[P,P-dimethyl-1,1'-phosphoniumdiylbis(2-methylbenzindenyl)zirconium dichloride] p-toluenesulfonate,

[P,P-dimethyl-1,1'-phosphoniumdiylbis(2-methylbenzindenyl)zirconium dichloride] tetrakispentafluorophenylborate,

[P,P-dimethyl-1,1'-phosphoniumdiyl(cyclopentadienyl)(fluoroenyl)zirconium dichloride] iodide and

[P,P-dimethyl-1,1'-phosphoniumdiylbis(2-methyl-4-tert-butylcyclopentadienyl)zirconium dichloride] iodide.

The preparation of the metallocene complexes I of the present invention can be carried out in such a way that the ligand systems II

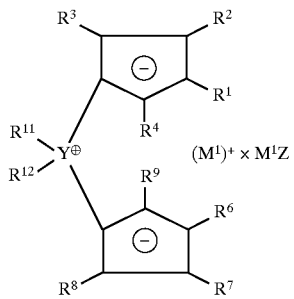

occur as intermediates. As regards the preferred substituents $R^1$ to $R^4$ and $R^6$ to $R^9$ and also $R^{11}$ and $R^{12}$, Y and Z, what has been said for the metallocene complexes I applies. $M^1$ is an alkali metal, preferably lithium or potassium.

A preferred process for preparing the metallocene complexes I and thus also for preparing the ligand systems II is as follows:

Compounds of the formula VI

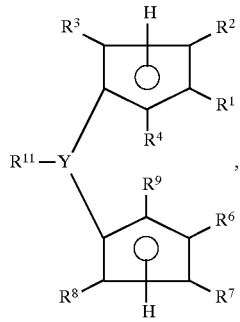

which are known per se or can be prepared by methods known per se, as described in Köpf et al., Monatshefte für Chemie 114 (1983), 243–247, are reacted with suitable metalating agents such as alkali metal hydrides or alkyls, preferably n-butyllithium, methyllithium or potassium hydride. This can likewise be carried out by the method described in Köpf et al., Monatshefte für Chemie 114 (1983), 243–247. This gives compounds of the formula III

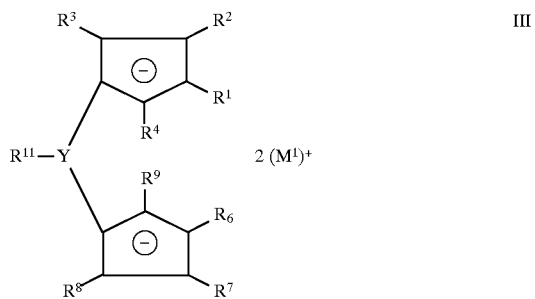

These compounds of the formula III can then be reacted with a quaternizing agent of the formula IV $$R^{12}-Z \qquad \text{IV,}$$

particular preference being given to methyl iodide, to give the ligand systems II. The reaction conditions are not critical per se. Preferably, III is admixed with organic solvents such as ethers or aromatic hydrocarbons, preferably toluene, and cooled to from −80° C. to 0° C. The quaternizing agent IV is then added and the mixture is warmed to room temperature.

Preferably, the ligand system II is not isolated but instead reacted immediately in solution with a metal compound of the formula V $$MX_{n+2} \qquad \text{V}$$

to give the metallocene complexes I of the present invention.

The reaction conditions for preparing the metallocene complexes I are likewise not critical. Preference is given to cooling the solution of II to from −80° C. to 0° C. and adding it to the metal compound V. After warming to room temperature, the resulting metallocene complex I is dried and, for example, washed with pentane.

The metallocene complexes I of the present invention can be used as catalysts for the polymerization of alkenes, in particular of alk-1-enes.

It is thus possible to prepare homopolymers and copolymers of $C_2$–$C_{10}$-alk-1-enes, with preferred monomers being ethylene, propylene, 1-butene, 1-pentene and 1-hexene.

However, cycloolefins or higher alk-1-enes and also alkenes in general can be used as monomers for the homopolymerization or copolymerization.

The preparation of the polymers can be carried out either batchwise or preferably continuously in the customary reactors used for the polymerization of alkenes. Suitable reactors are, inter alia, continuously operated loop reactors or stirred reactors; it is also possible to use a cascade of a plurality of stirred reactors connected in series or else high-pressure autoclaves or high-pressure tube reactors.

The polymerization conditions are not critical per se; pressures of from 0.5 to 3500 bar, preferably from 1 to 50 bar, and temperatures of from −60° C. to +200° C. have been found to be suitable.

Polymerization reactions using the metallocene complexes I of the present invention can be carried out in bulk, in the gas phase, in suspension and in inert solvents. Suitable suspension media or solvents are hydrocarbons, preferably $C_4$–$C_{10}$-alkanes.

Metallocene complexes are usually activated using compounds which form metallocenium ions, eg. Lewis acids, Brönsted acids or aluminoxanes such as methylaluminoxanes.

Furthermore, the bridging element in the metallocene complexes I of the present invention does not interact with the metal of the metallocene complex. In addition, there are no interactions with the Lewis acids customarily used in olefin polymerization, eg. aluminum alkyls or boron alkyls, which could lead to deactivation of the catalyst.

EXAMPLES

Example 1

Preparation of [P,P-dimethyl-1,1'-phosphoniumdiylbis(2-methyl-4-tert-butylcyclopentadienyl)zirconium dichloride] iodide I1

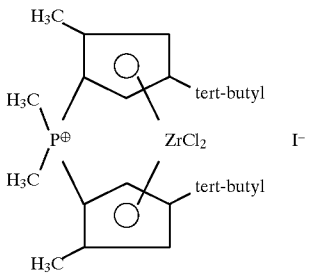

a) Preparation of the ligand system lithium P,P-dimethylbis (2-methyl-4-tert-butylcyclopentadienyl)phosphonium x lithium iodide II1

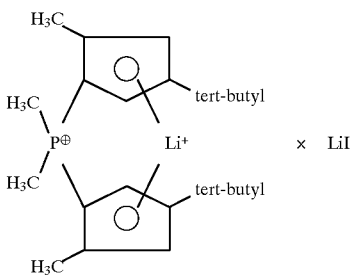

4.85 g of methyl-3-tert-butylcyclopentadienyllithium (34 mmol) were suspended in a solution of 30 ml of THF (tetrahydrofuran) and 10 ml of pentane. A solution of 1.5 ml of dichloromethylphosphine (16 mmol) in 6 ml of THF was slowly added dropwise at −40° C. to the above suspension. The initially orange suspension was allowed to warm to room temperature overnight. The reaction mixture was subsequently evaporated to dryness in a high vacuum, the resulting methylbis(2-methyl-4-tert-butylcyclopentadienyl) phosphine VI1

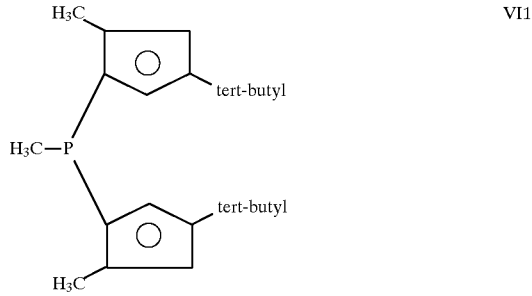

was taken up in pentane and separated from the lithium chloride by filtration.

| $^1$H-NMR (CDCl$_3$): | | |
|---|---|---|
| δ (ppm) | Splitting, intensity | Assignment |
| 6.21; 6.00; 5.77; 5.60 | m, 2H | olef. Cp-H |
| 3.01 | m, 4H | aliphat. Cp-H |
| 2.09–2.05 | plurality of s, 6H | Cp-Me |
| 1.38; 1.21 | d, 3H | P-Me, I$^2$ (P,H) = 2.4 Hz |
| 1.25–1.10 | plurality of s, 18H | Cp-tert-butyl |

12.8 ml of a 2.5 molar solution of n-butyllithium in hexane (32 mmol) were added dropwise at −50° C. to a solution of 5.06 g of methylbis(2-methyl-4-tert-butylcyclopentadienyl)phosphine VI1 (16 mmol) in pentane. The reaction mixture was allowed to warm to room temperature overnight and was evaporated to half its volume. This gave dilithium methylbis(2-methyl-4-tert-butylcyclopentadienyl)phosphine III1,

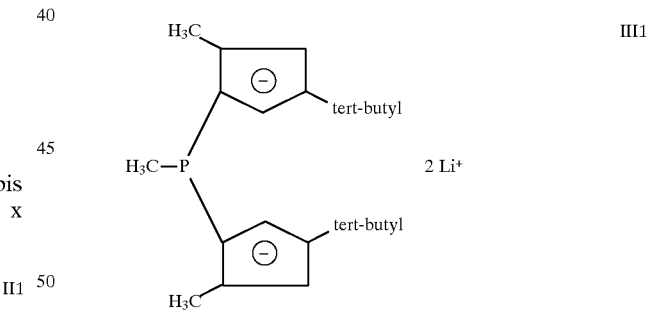

as a yellow, voluminous product.

The supernatant solution was separated off, the solid was washed with a little cold pentane and dried in a high vacuum.

Yield: 3.92 g (12 mmol) 75% based on methyl-3-tert-butyllithium.

0.5 ml of methyl iodide (8mmol) was added in three portions to a suspension of 0.98 g of dilithium methylbis (2-methyl-4-tertbutylcyclopentadienyl)phosphine III1 (2.98 mmol) in toluene at −10° C. The mixture was subsequently allowed to warm to room temperature overnight, giving a yellow suspension. The white solid was allowed to settle and the supernatant toluene solution was separated off. The resulting ligand system lithium P,P-dimethylbis-2-methyl-4-tert-butylcyclopentadienyl)phosphonium x lithium iodide II1 was not isolated but reacted further directly in solution.

| δ (ppm) | ¹H-NMR (CDCl₃): Splitting, intensity | Assignment |
|---|---|---|
| 5.97 | m, 4H | Cp-H |
| 2.34 | quat. 6H | Cp-Me |
| 2.07 | d, 6H | P-Me, I² (P,H) = 13.5 Hz |
| 1.25 | s, 18H | Cp-tert-butyl | b) Conversion of II1 to I1

A solution of 1 g of lithium P,P-dimethylbis(2-methyl-4-tertbutylcyclopentadienyl)phosphonium x lithium iodide II1 (2.98 mmol) in toluene was cooled to −10° C. This was added to 0.7 g of ZrCl₄ (2.98 mmol). On addition of the ligand salt, the reaction mixture suddenly became bright yellow. It was allowed to warm to room temperature overnight. The solid was dried in a high vacuum and washed with pentane. The metallocene complex I1 could not be separated from the lithium chloride formed.

| δ (ppm) | ¹H-NMR (CDCl₃): Splitting, intensity | Assignment |
|---|---|---|
| 6.82; 6.72; 6.42; 6.04 | m, 4H | Cp-H |
| 3.42; 3.22; 3.03 | 3 superimposed d, 6H | P-Me, J² (P,H) = 15 Hz |
| 2.38; 2.34 | 2 s, 6H | Cp-Me |
| 1.35; 1.32 | 2 s, 18H | Cp-tert-butyl |

| MS (FAB): | | |
|---|---|---|
| Fragment | m/e | Intensity |
| M⁺-ZrCl₄ | 331 | 100% |

Example 2

Preparation of polypropylene 20 ml of methylaluminoxane solution in toluene (1.53 molar, from Witco) were added at room temperature to a suspension of 12 mg of the mixture of compound I1 and lithium chloride as transition metal component in 20 ml of toluene and the resulting yellow-orange solution was pre-activated for 30 minutes. This solution was transferred to a 1 l glass autoclave charged with 500 ml of dry toluene. The autoclave was subsequently pressurized with propylene at room temperature while stirring to a pressure of 2 bar. This pressure was maintained for a total of 4 hours by further metering-in of propylene. The autoclave was subsequently vented and the mixture obtained was poured into a mixture of 700 ml of methanol and 30 ml of HCl (conc.). The precipitate was filtered off, washed with 50 ml of methanol and subsequently dried for 8 hours at 60° C./1 mbar in a vacuum drying oven. This gave 52.7 g of homopolypropylene having a melting point of Tm=151.2° C. and a molecular weight characterized by a weight average of $M_w$=42,500 and a number average of $M_n$=19,800, hence $M_w/M_n$=2.15.

Comparative Example C1

Preparation of P-methyl-1,1'-phosphinediylbis(2-methyl-4-tert-butylcyclopentadienyl)zirconium dichloride VII1

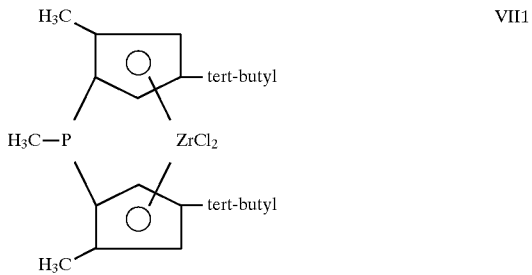

0.52 g of dilithium methylbis(2-methyl-4-tert-butylcyclopentadienyl)phosphine (1.6 mmol) III1 was mixed with 0.37 g of ZrCl₄ (1.6 mmol) and admixed with toluene. The mixture was stirred overnight at room temperature. The reaction mixture was evaporated to dryness, the complex was taken up in pentane and the lithium chloride formed was removed by filtration. The green pentane solution was evaporated to dryness in a high vacuum, leaving a fluorescent yellow solid.

Yield: 0.41 g (0.86 mmol)=54% based on the dilithium salt.

| δ (ppm) | ¹H-NMR (CDCl₃): Splitting, intensity | Assignment |
|---|---|---|
| 6.51; 6.29; 5.87; 5.71; 5.57 | m, 4H | Cp-H |
| 2.3–2.2 | plurality of s, 6H | Cp-Me |
| 1.97; 1.81 | d, 3H | P-Me, J² (P,H) = 5 Hz |
| 2.4–1.2 | plurality of s, 18H | Cp-tert-butyl |

Comparative Example C2

Preparation of polypropylene

Example 2 was repeated except that the transition metal component used was 8.2 mg (17.2 μmol) of compound VII1. No polymer could be isolated.

The weight average $M_w$ and the number average $M_n$ in Example 2 were determined by gel permeation chromatography and the melting point $T_m$ was determined by means of DSC (differential scanning calorimetry).

We claim:

1. A metallocene complex of the formula I

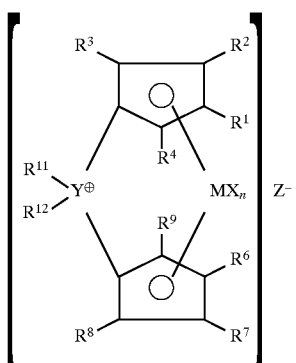

where the substituents have the following meanings:

M is a metal of transition group III, IV, V or VI of the Periodic Table of the Elements or a metal of the lanthanide group, X is fluorine, chlorine, bromine, iodine, hydrogen, $C_1$–$C_{10}$-alkyl, $C_6$–$C_{15}$-aryl or —$OR^5$, where $R^5$ is $C_1$–$C_{10}$-alkyl, $C_6$–$C_{15}$-aryl, alkylaryl, arylalkyl, fluoroalkyl or fluoroaryl each having from 1 to 10 carbon atoms in the alkyl radical and from 6 to 20 carbon atoms in the aryl radical, $R^1$ to $R^4$ and $R^6$ to $R^9$ are hydrogen, $C_1$–$C_{10}$-alkyl, 5- to 7-membered cycloalkyl which may in turn bear $C_1$–$C_{10}$-alkyls as substituents, $C_6$–$C_{15}$-aryl or arylalkyl, where two adjacent radicals may also together form a cyclic group having from 4 to 15 carbon atoms, or $Si(R^{10})_3$ where $R^{10}$ is $C_1$–$C_{10}$-alkyl, $C_6$–$C_{15}$-aryl or $C_3$–$C_{10}$-cycloalkyl, Y is nitrogen, phosphorus, arsenic, antimony or bismuth, $R^{11}$, $R^{12}$ are hydrogen, $C_1$–$C_{10}$-alkyl, $C_3$–$C_{10}$-cycloalkyl or $C_6$–$C_{15}$-aryl, n is 0, 1 or 2 and $Z^-$ is a halide, carboxylate, monosubstituted sulfonate, borate or alkoxide.

2. A ligand system of the formula II

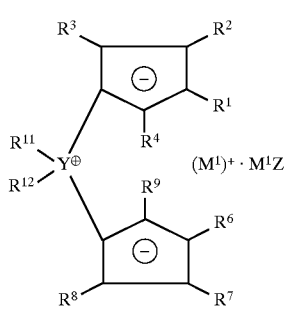

where the substituents have the following meanings:

$R^1$ to $R^4$ and $R^6$ to $R^9$ are hydrogen, $C_1$–$C_{10}$-alkyl, 5- to 7-membered cycloalkyl which may in turn bear $C_1$–$C_{10}$-alkyls as substituents, $C_6$–$C_{15}$-aryl or arylalkyl, where two adjacent radicals may also together form a cyclic group having from 4 to 15 carbon atoms, or $Si(R^{10})_3$ where $R^{10}$ is $C_1$–$C_{10}$-alkyl, $C_6$–$C_{15}$-aryl or $C_3$–$C_{10}$-cycloalkyl, Y is nitrogen, phosphorus, arsenic, antimony or bismuth, $R^{11}$, $R^{12}$ are hydrogen, $C_1$–$C_{10}$-alkyl, $C_3$–$C_{10}$-cycloalkyl or $C_6$–$C_{15}$-aryl, z is a halide, carboxylate, monosubstituted sulfonate, borate or alkoxide and $M^1$ is an alkali metal.

3. A process for preparing a ligand system II as defined in claim 2, which comprises reacting a compound of the formula III

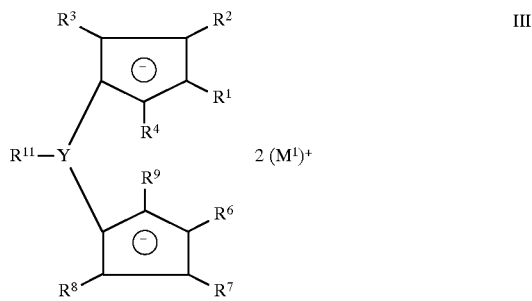

with a quaternizing agent of the formula IV

4. A process for preparing a metallocene complex I as defined in claim 1, which comprises reacting a ligand system of the formula II with a metal compound of the formula V

5. A process for polymerizing alkenes which comprises contacting said alkenes with a metallocene complex I as defined in claim 1 which is activated with compounds which form metallocenium ions.

* * * * *